US012583812B2

(12) United States Patent
Lyu et al.

(10) Patent No.: US 12,583,812 B2
(45) Date of Patent: Mar. 24, 2026

(54) METHOD FOR PREPARING ACRYLIC ACID

(71) Applicant: LG CHEM, LTD., Seoul (KR)

(72) Inventors: Byeong Gil Lyu, Daejeon (KR); Mi Kyung Kim, Daejeon (KR); Eun Kyo Kim, Daejeon (KR); Hye Bin Kim, Daejeon (KR)

(73) Assignee: LG CHEM, LTD., Seoul (KR)

( * ) Notice: Subject to any disclaimer, the term of this patent is extended or adjusted under 35 U.S.C. 154(b) by 552 days.

(21) Appl. No.: 18/265,543

(22) PCT Filed: Jun. 16, 2022

(86) PCT No.: PCT/KR2022/008575
§ 371 (c)(1),
(2) Date: Jun. 6, 2023

(87) PCT Pub. No.: WO2023/063525
PCT Pub. Date: Apr. 20, 2023

(65) Prior Publication Data
US 2024/0025833 A1      Jan. 25, 2024

(30) Foreign Application Priority Data

Oct. 15, 2021    (KR) ........................ 10-2021-0137933

(51) Int. Cl.
| | | |
|---|---|---|
| *C07C 51/377* | (2006.01) | |
| *B01D 3/14* | (2006.01) | |
| *B01J 19/00* | (2006.01) | |
| *C07C 51/44* | (2006.01) | |

(52) U.S. Cl.
CPC ............ *C07C 51/377* (2013.01); *B01D 3/143* (2013.01); *B01J 19/0013* (2013.01); *C07C 51/44* (2013.01); *B01J 2219/00087* (2013.01)

(58) Field of Classification Search
CPC ........ C07C 51/377; C07C 57/04; C07C 51/44
USPC ........................................................ 562/599
See application file for complete search history.

(56) References Cited

U.S. PATENT DOCUMENTS

| | | | |
|---|---|---|---|
| 6,596,129 | B1 | 7/2003 | Yoneda et al. |
| 2004/0260122 | A1 | 12/2004 | Yada et al. |
| 2006/0025629 | A1 | 2/2006 | Kang et al. |
| 2012/0226074 | A1 | 9/2012 | Ho et al. |
| 2014/0343320 | A1 | 11/2014 | Kang |
| 2017/0174604 | A1 | 6/2017 | Decourcy |
| 2017/0283358 | A1 | 10/2017 | Jain et al. |
| 2019/0071382 | A1 | 3/2019 | Fauconet et al. |

FOREIGN PATENT DOCUMENTS

| | | |
|---|---|---|
| JP | S60-104034 | 6/1985 |
| JP | 3246216 | 1/2002 |
| JP | 2005247714 A | 9/2005 |
| JP | 2008162956 A | 7/2008 |
| JP | 2008162957 A | 7/2008 |
| JP | 2009-242285 | 10/2009 |
| JP | 2012077014 A | 4/2012 |
| JP | 4942878 | 5/2012 |
| JP | 2013159586 A | 8/2013 |
| JP | 2013193970 A | 9/2013 |
| JP | 2014-189510 | 10/2014 |
| JP | 2019508477 A | 3/2019 |
| JP | 2019514937 A | 6/2019 |
| JP | 2023523616 A | 6/2023 |
| KR | 10-2001-0051479 | 6/2001 |
| KR | 10-2006-0048785 | 5/2006 |
| KR | 10-2013-0029703 | 3/2013 |
| KR | 10-2016-0122749 | 10/2016 |
| KR | 10-2017-0113177 | 10/2017 |
| KR | 10-2018-0064432 | 6/2018 |
| KR | 10-2018-0074314 | 7/2018 |
| WO | 2003-031384 | 4/2003 |

*Primary Examiner* — Ana Z Muresan

(74) *Attorney, Agent, or Firm* — Bryan Cave Leighton Paisner LLP

(57) ABSTRACT

Provided is a method for preparing an acrylic acid including: supplying a lactic acid aqueous solution to a reactor and performing a dehydration reaction to prepare a reaction product including an acrylic acid; supplying a reactor discharge stream including the reaction product to a first cooling tower and supplying an upper discharge stream from the first cooling tower to a second cooling tower; supplying a first acrylic acid aqueous solution stream discharged from a lower portion of the second cooling tower to an extraction column; supplying an upper discharge stream from the extraction column and a second acrylic acid aqueous solution stream discharged from a lower portion of the first cooling tower to a distillation column; and separating the acrylic acid from a lower discharge stream from the distillation column.

11 Claims, 2 Drawing Sheets

【FIG. 1】
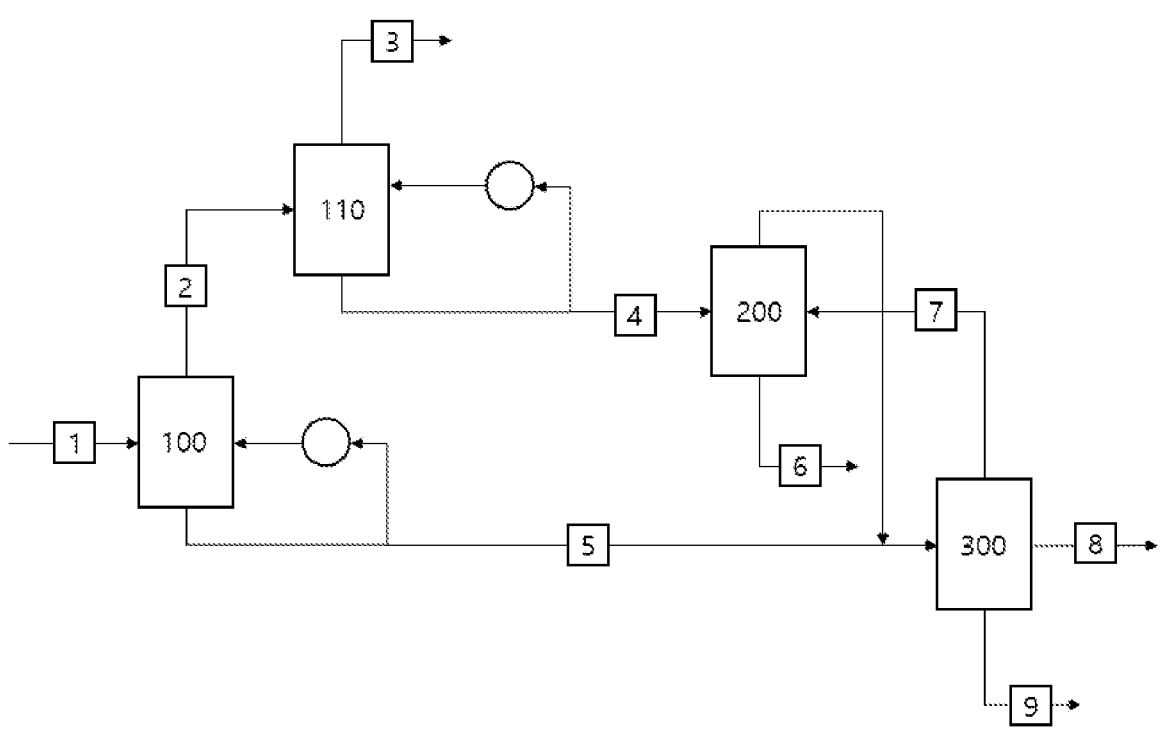
【FIG. 2】
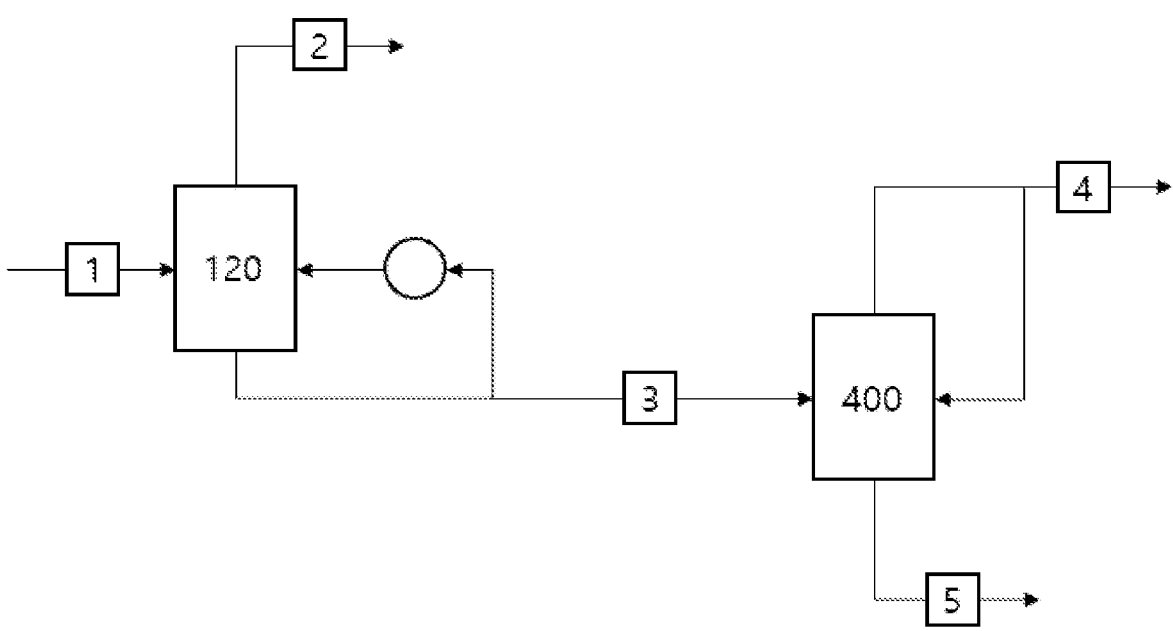

【FIG. 3】
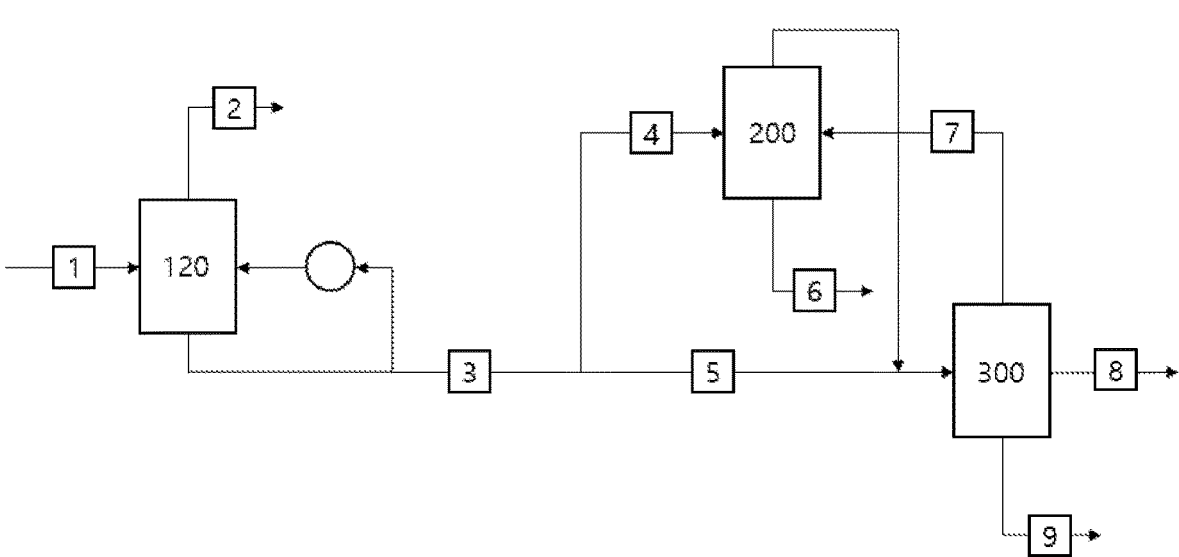

METHOD FOR PREPARING ACRYLIC ACID

CROSS-REFERENCE TO RELATED APPLICATIONS

The present application is a National Stage Application of International Application No. PCT/KR2022/008575 filed on Jun. 16, 2022, which claims the benefit of and priority to Korean Patent Application No. 10-2021-0137933, filed on Oct. 15, 2021, the entire contents of which are incorporated herein as a part of the specification.

TECHNICAL FIELD

The present invention relates to a method for preparing an acrylic acid, and more particularly, to a method for preparing an acrylic acid by a dehydration reaction of a lactic acid, which reduces energy used while reducing an acrylic acid loss.

BACKGROUND

An acrylic acid is used as a polymer raw material used in fiber, adhesives, paint, fiber processing, leather, building materials, and the like, and its demand is growing. In addition, the acrylic acid is also used as a raw material of an absorbent resin and is industrially used a lot in absorbent articles such as paper diapers and sanitary napkins, agricultural and horticultural water retaining agents, industrial water stop materials, and the like.

A conventional method for preparing an acrylic acid is generally a method of oxidizing propylene in the air, but the method is a method of converting propylene into acrolein by a gaseous contact oxidation reaction and subjecting the acrolein to a gaseous contact oxidation reaction to prepare an acrylic acid, and the method produces an acetic acid as a by-product, which is difficult to separate from the acrylic acid. In addition, the method for preparing an acrylic acid using propylene uses propylene obtained by refining crude oil which is a fossil resource, as a raw material, and considering problems such as a recent rise in crude oil prices or global warming, the method has a problem in terms of raw material costs or environmental pollution.

Thus, a study on a method for preparing an acrylic acid from a carbon-neutral biomass raw material was conducted. For example, there is a method for preparing an acrylic acid (AA) by a gaseous dehydration reaction of a lactic acid (LA). This method is generally a method for preparing an acrylic acid by an intramolecular dehydration reaction of a lactic acid in the presence of a catalyst at a high temperature of 300° C. or higher. In this case, when the lactic acid is used at a high concentration, oligomers such as dimers and trimers are produced to lower the concentration of the lactic acid participating in the reaction. In addition, when the concentration of the lactic acid is lowered, the amount of water is large, and thus, the amount of energy used for removing water is increased.

BRIEF DESCRIPTION

Technical Problem

An object of the present invention is to provide a method of reducing energy required to separate and remove water and minimizing an acrylic acid loss, in preparing an acrylic acid by a dehydration reaction of a lactic acid, in order to solve the problems mentioned in the Background Art.

Technical Solution

In one general aspect, provided is a method for preparing an acrylic acid, the method including: supplying a lactic acid aqueous solution to a reactor and performing a dehydration reaction to prepare a reaction product including an acrylic acid; supplying a reactor discharge stream including the reaction product to a first cooling tower and supplying an upper discharge stream from the first cooling tower to a second cooling tower; supplying a first acrylic acid aqueous solution stream discharged from a lower portion of the second cooling tower to an extraction column; supplying an upper discharge stream from the extraction column and a second acrylic acid aqueous solution stream discharged from a lower portion of the first cooling tower to a distillation column; and separating the acrylic acid from a lower discharge stream from the distillation column.

Advantageous Effects

According to the method for preparing an acrylic acid of the present invention, the amount of energy used for separating water can be reduced and also an acrylic acid loss can be decreased, by separating a reaction product including an acrylic acid into a first acrylic acid aqueous solution stream and a second acrylic acid aqueous solution stream which have a composition advantageous for separation in each of a distillation column and an extraction column, using two cooling towers, and supplying the streams to the extraction column and the distillation column, respectively.

DESCRIPTION OF THE DRAWINGS

FIG. 1 is a process flow diagram of a method for preparing an acrylic acid according to an exemplary embodiment of the present invention.

FIGS. 2 and 3 are process flow diagrams of methods of preparing an acrylic acid according to the comparative examples, respectively.

DETAILED DESCRIPTION

The terms and words used in the description and claims of the present invention are not to be construed limitedly as having general or dictionary meanings but are to be construed as having meanings and concepts meeting the technical ideas of the present invention, based on a principle that the inventors are able to appropriately define the concepts of terms in order to describe their own inventions in the best mode.

The term "stream" in the present invention can refer to a fluid flow in a process, or can refer to a fluid itself flowing in a pipe. Specifically, the stream can refer to both a fluid itself flowing in a pipe connecting each device and a fluid flow. In addition, the fluid can include any one or more components of gas, liquid, and solid.

Hereinafter, the present invention will be described in more detail for better understanding of the present invention, with reference to FIG. 1.

According to the present invention, a method for preparing an acrylic acid is provided. More specifically, the method can include: supplying a lactic acid aqueous solution to a reactor and performing a dehydration reaction to prepare a reaction product including an acrylic acid; supplying a reactor discharge stream including the reaction product to a first cooling tower 100 and supplying an upper discharge stream from the first cooling tower 100 to a second cooling tower 110; supplying a first acrylic acid aqueous solution stream discharged from a lower portion of the second cooling tower 110 to an extraction column 200; supplying an upper discharge stream from the extraction column 200 and a second acrylic acid aqueous solution stream discharged from a lower portion of the first cooling tower 100 to a distillation column 300; and separating the acrylic acid from a lower discharge stream from the distillation column 300.

Specifically, a conventional method for preparing an acrylic acid is generally a method of oxidizing propylene in the air, but the method is a method of converting propylene into acrolein by a gaseous contact oxidation reaction and subjecting the acrolein to a gaseous contact oxidation reaction to prepare an acrylic acid, and the method produces an acetic acid as a by-product, which is difficult to separate from the acrylic acid. In addition, the method for preparing an acrylic acid using propylene uses propylene obtained by refining crude oil which is a fossil resource, as a raw material, and considering problems such as a recent rise in crude oil prices or global warming, the method has a problem in terms of raw material costs or environmental pollution.

In order to solve the problems of the conventional method for preparing an acrylic acid, a study on a method for preparing an acrylic acid from a carbon-neutral biomass raw material was conducted. For example, there is a method for preparing an acrylic acid (AA) by a gaseous dehydration reaction of a lactic acid (LA). This method is generally a method for preparing an acrylic acid by an intramolecular dehydration reaction of a lactic acid in the presence of a catalyst at a high temperature. However, when a high concentration of a lactic acid aqueous solution is used as a raw material, oligomers such as dimers and trimers are formed by an equilibrium reaction to lower the content of a lactic acid monomer participating in the reaction, and when the concentration of the lactic acid aqueous solution is lowered and used as a raw material, the content of water in a reaction product of a lactic acid dehydration reaction is significantly higher than that in a conventional process of preparing an acrylic acid by a propylene oxidation reaction, and thus, the amount of energy used required for water separation is greatly increased.

In this regard, in order to solve the conventional problems, the present invention is intended to provide a method for preparing an acrylic acid by a dehydration reaction of a lactic acid, which reduces the amount of energy used required for water separation and also minimizes an acrylic acid loss.

According to an exemplary embodiment of the present invention, a lactic acid is supplied to a reactor and a dehydration reaction is performed to prepare a reaction product including an acrylic acid. Here, the lactic acid can be introduced to the reactor in an aqueous solution state, and the dehydration reaction can be performed in a gaseous reaction in the presence of a catalyst. For example, the concentration of the lactic acid in the lactic acid aqueous solution can be 10 wt % or more, 20 wt % or more, or 30 wt % or more and 40 wt % or less, 50 wt % or less, 60 wt % or less, or 70 wt % or less.

The reactor can be a reactor capable of a common dehydration reaction of a lactic acid, the reactor can include a reaction tube filled with a catalyst, and while a reaction gas including volatile components of a lactic acid aqueous solution as a raw material is passed through the reaction tube, a lactic acid can be dehydrated by a gaseous contact reaction to produce an acrylic acid. The reaction gas can further include any one or more dilution gases of water vapor, nitrogen gas, and air for adjusting a concentration, in addition to the lactic acid.

Operation conditions of the reactor can be common dehydration reaction conditions of a lactic acid. Here, the operation temperature of the reactor can refer to a set temperature of a heating medium or the like used for controlling the temperature of the reactor.

A catalyst used in the dehydration reaction of the lactic acid can include, for example, one or more selected from the group consisting of sulfate-based catalysts, phosphate-based catalysts, and nitrate-based catalysts. As a specific example, the sulfate can include $Na_2SO_4$, $K_2SO_4$, $CaSO_4$, and $Al_2(SO_4)_3$, the phosphate can include $Na_3PO_4$, $Na_2HPO_4$, $NaH_2PO_4$, $K_3PO_4$, $K_2HPO_4$, $KH_2PO_4$, $CaHPO_4$, $Ca_3(PO_4)_2$, $AlPO_4$, $CaH_2P_2O_7$, and $Ca_2P_2O_7$, and the nitrate can include $NaNO_3$, $KNO_3$, and $Ca(NO_3)_2$. In addition, the catalyst can be supported on a support. The support can include one or more selected from the group consisting of, for example, diatomaceous earth, alumina, silica, titanium dioxide, carbides, and zeolite.

A reaction product prepared from the dehydration reaction of the lactic acid can further include by-products such as water ($H_2O$), acetaldehyde (ACHO), carbon monoxide (CO), carbon dioxide ($CO_2$), and low-boiling point materials and high-boiling point materials of dilution gas, in addition to the acrylic acid as a product to be desired.

A content ratio of water to the acrylic acid in the reaction product can be 2.0 or more, 2.3 or more, or 2.5 or more and 2.6 or less, 3.0 or less, 3.3 or less, or 3.5 or less. When a reaction product having the content ratio of water to the acrylic acid within the range is prepared and the acrylic acid is separated from the reaction product by the method according to the present invention, water is effectively separated using less energy and an acrylic acid loss is reduced to increase a recovery rate.

According to an exemplary embodiment of the present invention, a reactor discharge stream including the reaction product can be supplied to a first cooling tower 100 and cooled. Specifically, since the reactor discharge stream including the reaction product is discharged in a gas phase, it can be supplied to the first cooling tower 100 and condensed. A condensate condensed in this process can be discharged as a lower discharge stream from the first cooling tower 100, and an upper discharge stream from the first cooling tower 100 including gaseous components can be supplied to a second cooling tower 110.

A part of the stream of a lower discharge stream from the first cooling tower 100 can be refluxed to the first cooling tower 100 via a cooler, and the rest of the stream can be supplied to a distillation column 300 as a second acrylic acid aqueous solution stream.

The upper discharge stream from the first cooling tower 100 can include water, an acrylic acid, and gas components, the second acrylic acid aqueous solution stream can include water and an acrylic acid, and the upper discharge stream from the first cooling tower 100 can have a higher content of water and a lower content of the acrylic acid than the second acrylic acid aqueous solution stream.

A content ratio of water to the acrylic acid in the second acrylic acid aqueous solution stream can be for example, 1.0 or more, 1.2 or more, or 1.4 or more and 1.8 or less, 1.9 or less, 2.0 or less, or 2.1 or less. By controlling the composition of the second acrylic acid aqueous solution stream to be within the above range, it can be advantageous in terms of energy and prevention of acrylic acid loss in separation by supplying to the distillation column 300 without passing through an extraction column 200.

According to an exemplary embodiment of the present invention, the upper discharge stream 2 from the first cooling tower 100 can be supplied to a second cooling tower 110, and the gas components 3 can be removed in the second cooling tower 110. Specifically, the upper discharge stream 2 from the first cooling tower 100 supplied to the second cooling tower 110 is gaseous components, and can be condensed in the second cooling tower 110. In this process, the condensed condensate can be discharged to the lower portion of the second cooling tower 110 as the first acrylic acid aqueous solution stream 4 and supplied to the extraction column 200. Specifically, a part of the first acrylic acid aqueous solution stream 4 can be refluxed to the second cooling tower 110 through a cooler and the rest of the stream 4 can be supplied to the extraction column 200.

In addition, in the second cooling tower 110, the gas components 3 can be removed by separation in the upper portion, and the gas components can include acetaldehyde, with water, carbon monoxide, carbon dioxide, and a dilution gas. When the gas components are separated to the upper portion of the second cooling tower 110, a small amount of an acrylic acid can be separated together, and in the present invention, the reaction product including the acrylic acid is separated using two cooling towers, thereby minimizing the content of the acrylic acid which is discharged with the gas components and lost.

The operation temperature of the second cooling tower 110 can be 40° C. or higher, 50° C. or higher, or 60° C. or higher and 130° C. or lower, 150° C. or lower, or 200° C. or lower, and the operation pressure can be 1 kg/cm$^2$ or more, 1.5 kg/cm$^2$ or more, or 2 kg/cm$^2$ or more and 5 kg/cm$^2$ or less, 10 kg/cm$^2$ or less, or 20 kg/cm$^2$ or less. The operation conditions of the second cooling tower 110 are controlled to the operation temperature and the operation pressure within the above range, thereby controlling the composition of the gas components separated to the upper portion of the second cooling tower 110 to minimize an acrylic acid loss and removing the dilution gas and acetaldehyde out of the system, and controlling the composition of the first acrylic acid aqueous solution stream discharged from the lower portion of the second cooling tower 110.

A content ratio of water to the acrylic acid in the first acrylic acid aqueous solution stream 4 can be, for example, 3.0 or more, 3.1 or more, 3.2 or more, or 3.3 or more and 3.8 or less, 4.0 or less, or 4.5 or less. The composition of the first acrylic acid aqueous solution stream is controlled to be within the above range, thereby controlling the composition of the first acrylic acid aqueous solution stream to an advantageous composition in terms of energy and prevention of acrylic acid loss when separation is performed by supplying to the distillation column 300 after passing through the extraction column 200.

According to an exemplary embodiment of the present invention, the first acrylic acid aqueous solution stream is supplied to the extraction column 200, and in the extraction column 200, the acrylic acid and water can be separated using an extractant. Specifically, an extractant can be supplied to the extraction column 200, and the extractant can include one or more selected from the group consisting of, for example, benzene, toluene, xylene, n-heptane, cycloheptane, cycloheptene, 1-heptene, ethylbenzene, methylcyclohexane, n-butylacetate, isobutylacetate, isobutylacrylate, n-propylacetate, isopropylacetate, methylisobutylketone, 2-methyl-1-heptene, 6-methyl-1-heptene, 4-methyl-1-heptene, 2-ethyl-1-hexene, ethylcyclopentane, 2-methyl-1-hexene, 2,3-dimethylpentane, 5-methyl-1-hexene, and isopropylbutylether. As a specific example, the extractant can be toluene.

In the extraction column 200, the first acrylic acid aqueous solution stream and the extractant are brought into contact and an extract and an extraction residue solution can be separated. For example, the extract can be an acrylic acid dissolved in the extractant, and the extract can be discharged as an upper discharge stream from the extraction column 200. In addition, the extraction residue solution is wastewater including water and can be separated as a lower discharge stream 6 from the extraction column 200. Here, the lower discharge stream 6 from the extraction column 200 can include a small amount of an acrylic acid in addition to water, and in the present invention, the reaction product including the acrylic acid is separated into the first acrylic acid aqueous solution stream and the second acrylic acid aqueous solution stream which have advantageous compositions for separation in the distillation column 300 and the extraction column 200, respectively, using two cooling towers, and the streams are supplied to the extraction column 200 and the distillation column 300, respectively, thereby minimizing an acrylic acid loss included in wastewater and discharged.

According to an exemplary embodiment of the present invention, the upper discharge stream from the extraction column 200 and the second acrylic acid aqueous solution stream discharged from the lower portion of the first cooling tower 100 can be supplied to the distillation column 300, and components can be separated by distillation.

The upper discharge stream from the extraction column 200 and the second acrylic acid aqueous solution stream can form a mixed stream and be supplied to the distillation column 300. The mixed stream having the flow ratio within the range is supplied to the distillation column 300, thereby decreasing the amount of energy used required for separation in the distillation column 300, and separating water and the acrylic acid using the extractant included in the upper discharge stream from the extraction column 200 without using an additional azeotropic agent.

In the distillation column 300, the extractant included in the mixed stream can be separated to the upper portion as stream 7, circulated to the extraction column 200, and reused. In addition, in the distillation column 300, the acrylic acid included in the mixed stream is separated as a lower discharge stream 9, and water can be separated as a side discharge stream 8.

The operation temperature of the distillation column 300 can be 10° C. or higher, 20° C. or higher, or 40° C. or higher and 100° C. or lower, 120° C. or lower, or 150° C. or lower, and the operation pressure can be 10 torr or more, 50 torr or more, or 100 torr or more and 200 torr or less, 300 torr or less, or 500 torr or less. The operation conditions of the distillation column 300 are controlled to the operation temperature and the operation pressure within the above range, thereby effectively separating the extractant from the upper portion, water from the side portion, and the acrylic acid from the lower portion of the distillation column 300.

The lower discharge stream from the distillation column 300 can include an acrylic acid and a small amount of by-products. Therefore, if necessary, the lower discharge stream from the distillation column 300 is supplied to the refining unit to remove the by-products, thereby obtaining a high-purity acrylic acid.

According to an exemplary embodiment of the present invention, in the method for preparing an acrylic acid, if necessary, devices such as a distillation column, a condenser, a reboiler, a valve, a pump, a separator, a mixer, and the like can be further installed.

Hereinabove, the method for preparing an acrylic acid according to the present invention has been described and illustrated in the drawings, but the description and the illustration in the drawings are the description and the illustration of only core constitutions for understanding of the present invention, and in addition to the process and devices described above and illustrated in the drawings, the process and the devices which are not described and illustrated can be appropriately applied and used for carrying out the method for preparing an acrylic acid according to the present invention.

Hereinafter, the present invention will be described in more detail by the examples. However, the following examples are provided for illustrating the present invention, and it is apparent to a person skilled in the art that various modifications and alterations can be made without departing from the scope and spirit of the present invention and the scope of the present invention is not limited thereto.

aqueous solution stream, was supplied to the extraction column 200. At this time, the operation temperature of the second cooling tower 110 was controlled to 88° C. in the upper portion and 113° C. in the lower portion, and the operation pressure was controlled to 2 kg/cm$^2$.

In the extraction column 200, toluene was used as an extractant to dissolve the acrylic acid, which was separated as the upper discharge stream from the extraction column 200, and water was separated as the lower discharge stream.

The upper discharge stream from the extraction column 200 and the second acrylic acid aqueous solution stream formed a mixed stream and were supplied to the distillation column 300.

In the distillation column 300, the extractant was separated to the upper portion and refluxed to the extraction column 200, and a side discharge stream including water and a lower discharge stream including the acrylic acid were separated.

At this time, a flow rate (kg/hr) for each component in each stream is shown in the following Table 1:

TABLE 1

|  | 1 | 2 | 3 | 4 | 5 | 6 | 7 | 8 | 9 |
|---|---|---|---|---|---|---|---|---|---|
| $N_2$ | 101.2 | 101.2 | 101.2 | 0.0 | 0.0 | 0.0 | 0.0 | 0.0 | 0.0 |
| $CO/CO_2$ | 28.5 | 28.5 | 28.5 | 0.0 | 0.0 | 0.0 | 0.0 | 0.0 | 0.0 |
| ACHO | 14.0 | 13.8 | 13.6 | 0.2 | 0.1 | 0.2 | 2.6 | 0.2 | 0.0 |
| $H_2O$ | 597.3 | 309.7 | 38.5 | 271.1 | 287.6 | 268.2 | 0.6 | 290.5 | 0.0 |
| AA | 240.5 | 80.8 | 6.4 | 74.4 | 159.7 | 4.4 | 0.4 | 0.3 | 229.4 |
| By-product | 18.5 | 7.9 | 0.9 | 7.0 | 10.6 | 1.9 | 3.8 | 2.0 | 13.7 |
| Toluene | 0.0 | 0.0 | 0.0 | 0.0 | 0.0 | 0.2 | 781.9 | 0.2 | 0.0 |
| Total | 1000.0 | 541.9 | 189.1 | 352.7 | 458.0 | 274.9 | 789.3 | 293.2 | 243.1 |

EXAMPLES

Example 1

According to the process flow diagram illustrated in FIG. 1, a process of preparing an acrylic acid was simulated, using an Aspen Plus simulator from Aspen Technology, Inc.

Specifically, a lactic acid aqueous solution and nitrogen ($N_2$) as a dilution gas were supplied to a reactor to prepare a reaction product including an acrylic acid (AA) by a dehydration reaction, and at this time, a content ratio of water to the acrylic acid in the reaction product was adjusted to 2.5.

The reactor discharge stream including the reaction product was supplied to the first cooling tower 100, a part of the stream of a lower discharge stream from the first cooling tower 100 was refluxed to the first cooling tower 100 through a cooler, and the rest of the stream, that is, a second acrylic acid aqueous solution stream was supplied to a distillation column 300. At this time, the operation temperature of the first cooling tower 100 was controlled to 114° C. in the upper portion and 117° C. in the lower portion, and the operation pressure was controlled to 2 kg/cm$^2$.

The reactor discharge stream was condensed in the first cooling tower 100, the upper discharge stream from the first cooling tower 100 was supplied to a second cooling tower 110, gas components were discharged from the upper portion of the second cooling tower 110, a part of the stream of the lower discharge stream of the second cooling tower 110 was refluxed to the second cooling tower 110 through the cooler, and the rest of the stream, that is, the first acrylic acid The total is a value obtained by rounding the value determined in the Aspen Plus simulator to one decimal place.

Referring to Table 1, it was confirmed in Example 1 that the content ratio of water to the acrylic acid in the first acrylic acid aqueous solution stream was 3.6, the content ratio of water to the acrylic acid in the second acrylic acid aqueous solution stream was 1.8, the amount of acrylic acid loss when gas components were separated to the upper portion of the second cooling tower 110 was 6.4 kg/hr, and the amount of acrylic acid loss when water was removed from the lower portion of the extraction column 200 was 4.4 kg/hr.

In addition, the amount of energy used in the distillation column 300 was confirmed to be 0.370 Gcal/hr.

In addition, the recovery rate of the acrylic acid of Example 1, which was calculated by a ratio of the flow rate of the acrylic acid in the lower discharge stream from the distillation column 300 to the flow rate of the acrylic acid in the reactor discharge stream, was 95.4%.

Example 2

According to the process flow diagram illustrated in FIG. 1, a process of preparing an acrylic acid was simulated, using an Aspen Plus simulator from Aspen Technology, Inc.

Specifically, a lactic acid aqueous solution was supplied to a reactor to prepare a reaction product including an acrylic acid (AA) by a dehydration reaction, and at this time, a content ratio of water to the acrylic acid in the reaction product was adjusted to 3.

The reactor discharge stream including the reaction product was supplied to the first cooling tower 100, a part of the stream of a lower discharge stream from the first cooling tower 100 was refluxed to the first cooling tower 100 through a cooler, and the rest of the stream, that is, a second acrylic acid aqueous solution stream was supplied to a distillation column 300. At this time, the operation temperature of the first cooling tower 100 was controlled to 126° C. in the upper portion and 127° C. in the lower portion, and the operation pressure was controlled to 3 kg/cm².

The reactor discharge stream was condensed in the first cooling tower 100, the upper discharge stream from the first cooling tower 100 was supplied to a second cooling tower 110, gas components were discharged from the upper portion of the second cooling tower 110, a part of the stream of the lower discharge stream of the second cooling tower 110 was refluxed to the second cooling tower 110 through the cooler, and the rest of the stream, that is, the first acrylic acid aqueous solution stream was supplied to the extraction column 200. At this time, the operation temperature of the second cooling tower 110 was controlled to 109° C. in the upper portion and 122° C. in the lower portion, and operation pressure was controlled to 3 kg/cm².

In the extraction column 200, toluene was used as an extractant to dissolve the acrylic acid, which was separated as the upper discharge stream from the extraction column 200, and water was separated as the lower discharge stream.

The upper discharge stream from the extraction column 200 and the second acrylic acid aqueous solution stream formed a mixed stream and was supplied to the distillation column 300.

In the distillation column 300, the extractant was separated to the upper portion and refluxed to the extraction column 200, and a side discharge stream including water and a lower discharge stream including the acrylic acid were separated.

At this time, a flow rate (kg/hr) for each component in each stream is shown in the following Table 2:

TABLE 2

|  | 1 | 2 | 3 | 4 | 5 | 6 | 7 | 8 | 9 |
|---|---|---|---|---|---|---|---|---|---|
| $N_2$ | 0.0 | 0.0 | 0.0 | 0.0 | 0.0 | 0.0 | 0.0 | 0.0 | 0.0 |
| $CO/CO_2$ | 27.7 | 27.7 | 27.7 | 0.0 | 0.0 | 0.0 | 0.0 | 0.0 | 0.0 |
| ACHO | 13.6 | 13.5 | 13.3 | 0.2 | 0.1 | 0.2 | 2.8 | 0.1 | 0.0 |
| H2O | 702.0 | 404.7 | 30.3 | 374.3 | 297.3 | 370.8 | 0.9 | 300.9 | 0.0 |
| AA | 234.0 | 98.1 | 4.9 | 93.2 | 135.9 | 5.2 | 0.6 | 0.4 | 223.5 |
| By-product | 22.7 | 11.2 | 0.8 | 10.4 | 11.5 | 4.7 | 9.6 | 3.7 | 13.5 |
| Toluene | 0.0 | 0.0 | 0.0 | 0.0 | 0.0 | 0.3 | 1092.3 | 0.2 | 0.0 |
| Total | 1000.0 | 555.2 | 77.0 | 478.1 | 444.8 | 381.2 | 1106.2 | 305.3 | 237.0 |

Referring to Table 2, it was confirmed in Example 2 that the content ratio of water to the acrylic acid in the first acrylic acid aqueous solution stream was 4.0, the content ratio of water to the acrylic acid in the second acrylic acid aqueous solution stream was 2.2, the amount of acrylic acid loss when gas components were separated to the upper portion of the second cooling tower 110 was 4.9 kg/hr, and the amount of acrylic acid loss when water was removed from the lower portion of the extraction column 200 was 5.2 kg/hr.

In addition, the amount of energy used in the distillation column 300 was confirmed to be 0.458 Gcal/hr.

In addition, the recovery rate of the acrylic acid in Example 2 was 95.5%.

COMPARATIVE EXAMPLES

Comparative Example 1

According to the process flow diagram illustrated in FIG. 2, a process of preparing an acrylic acid was simulated, using an Aspen Plus simulator from Aspen Technology, Inc.

Specifically, a lactic acid aqueous solution and nitrogen ($N_2$) as a dilution gas were supplied to a reactor to prepare a reaction product including an acrylic acid (AA) by a dehydration reaction, and at this time, a content ratio of water to the acrylic acid in the reaction product was adjusted to 2.5.

A reactor discharge stream 1 including the reaction product was supplied to the cooling tower 120, a part of the lower discharge stream from the cooling tower 120 was refluxed to the cooling tower 120 through a cooler, the rest of the stream 3 was supplied to an azeotropic distillation column 400, and gas components were discharged as stream 2 from the upper portion of the cooling tower 120. At this time, the operation temperature of the cooling tower 120 was controlled to 89° C. in the upper portion and 117° C. in the lower portion, and the operation pressure was controlled to 2 kg/cm².

In the azeotropic distillation column 400, toluene was used as an azeotropic agent, the azeotropic agent was separated from the upper discharge stream and refluxed to the azeotropic distillation column 400, water was separated as the remaining stream 4, and the lower discharge stream 5 including an acrylic acid was separated.

At this time, a flow rate (kg/hr) for each component in each stream is shown in the following Table 3:

TABLE 3

|  | 1 | 2 | 3 | 4 | 5 |
|---|---|---|---|---|---|
| $N_2$ | 101.2 | 101.2 | 0.0 | 0.0 | 0.0 |
| $CO/CO_2$ | 28.5 | 28.5 | 0.0 | 0.0 | 0.0 |

TABLE 3-continued

|  | 1 | 2 | 3 | 4 | 5 |
|---|---|---|---|---|---|
| ACHO | 14.0 | 13.7 | 0.2 | 0.3 | 0.0 |
| H2O | 597.2 | 38.9 | 558.3 | 558.3 | 0.0 |
| AA | 240.5 | 8.2 | 232.3 | 2.0 | 230.3 |
| By-product | 18.5 | 0.9 | 17.6 | 3.9 | 13.7 |
| Toluene | 0.0 | 0.0 | 0.0 | 0.4 | 0.0 |
| Total | 999.9 | 191.4 | 808.4 | 564.9 | 244.0 |

Referring to Table 3, it was confirmed in Comparative Example 1 that the content ratio of water to the acrylic acid in the stream supplied to the azeotropic distillation column 400 was 2.4, the amount of acrylic acid loss when the gas components were separated to the upper portion of the cooling tower 120 was 8.2 kg/hr, and the amount of acrylic acid loss when water was removed from the upper portion of the azeotropic distillation column 400 was 2.0 kg/hr.

In addition, the amount of energy used in the azeotropic distillation column 400 was confirmed to be 0.697 Gcal/hr.

refluxed to the extraction column 200, and a side discharge stream 8 including water and a lower discharge stream 9 including an acrylic acid were separated.

At this time, a flow rate (kg/hr) for each component in each stream is shown in the following Table 4:

TABLE 4

|  | 1 | 2 | 3 | 4 | 5 | 6 | 7 | 8 | 9 |
|---|---|---|---|---|---|---|---|---|---|
| $N_2$ | 101.2 | 101.2 | 0.0 | 0.0 | 0.0 | 0.0 | 0.0 | 0.0 | 0.0 |
| $CO/CO_2$ | 28.5 | 28.5 | 0.0 | 0.0 | 0.0 | 0.0 | 0.0 | 0.0 | 0.0 |
| ACHO | 14.0 | 13.7 | 0.2 | 0.1 | 0.1 | 0.1 | 1.7 | 0.1 | 0.0 |
| $H_2O$ | 597.3 | 38.9 | 558.4 | 287.6 | 270.8 | 266.2 | 0.6 | 292.2 | 0.0 |
| AA | 240.5 | 8.2 | 232.4 | 119.7 | 112.7 | 11.4 | 0.3 | 0.3 | 220.6 |
| By-product | 18.5 | 0.9 | 17.6 | 9.1 | 8.5 | 1.9 | 3.7 | 1.9 | 13.7 |
| Toluene | 0.0 | 0.0 | 0.0 | 0.0 | 0.0 | 0.2 | 781.9 | 0.2 | 0.0 |
| Total | 1000.0 | 191.4 | 808.6 | 416.5 | 392.1 | 279.8 | 788.2 | 294.7 | 234.3 |

In addition, the recovery rate of the acrylic acid of Comparative Example 1, which was calculated by a ratio of the flow rate of the acrylic acid in the lower discharge stream from the azeotropic distillation column 400 to the flow rate of the acrylic acid in the reactor discharge stream, was 95.8%.

In this case, it was confirmed that the total amount of the lower discharge stream from the cooling tower 120 was supplied to the azeotropic distillation column 400 and water and an acrylic acid were azeotropically distilled, thereby increasing the amount of energy used in the azeotropic distillation column 400 as compared with Examples 1 and 2.

Comparative Example 2

According to the process flow diagram illustrated in FIG. 3, a process of preparing an acrylic acid was simulated, using an Aspen Plus simulator from Aspen Technology, Inc.

Specifically, a lactic acid aqueous solution and nitrogen ($N_2$) as a dilution gas were supplied to a reactor to prepare a reaction product including an acrylic acid (AA) by a dehydration reaction, and at this time, a content ratio of water to the acrylic acid in the reaction product was adjusted to 2.5.

The reactor discharge stream 1 including the reaction product was supplied to the cooling tower 120, a part of the stream 3 of the lower discharge stream from the cooling tower 120 was refluxed to the cooling tower 120 through a cooler, the rest of the stream was split into a first stream 4 and a second stream 5, and the first stream 4 was supplied to an extraction column 200 and the second stream 5 was supplied to a distillation column 300. In addition, gas components were discharged from the upper portion of the cooling tower 120 as stream 2. At this time, the operation temperature of the cooling tower 120 was controlled to 89° C. in the upper portion and 117° C. in the lower portion, and the operation pressure was controlled to 2 kg/cm².

In the extraction column 200, toluene was used as an extractant to dissolve the acrylic acid, which was separated as the upper discharge stream from the extraction column 200, and water was separated as the lower discharge stream 6.

The upper discharge stream from the extraction column 200 was supplied to the distillation column 300 with the second stream 5, an extractant was separated to the upper portion in the distillation column 300 as stream 7 and Referring to Table 4, it was confirmed in Comparative Example 2 that the content ratios of water to the acrylic acid in the stream supplied to the extraction column 200 and the stream supplied to the distillation column 300 were the same at 2.4, the amount of acrylic acid loss when the gas components were separated to the upper portion of the cooling tower 120 was 8.2 kg/hr, and the amount of acrylic acid loss when water was removed from the upper portion of the extraction column 200 was 11.4 kg/hr.

In addition, the amount of energy used in the distillation column 300 was confirmed to be 0.380 Gcal/hr.

In addition, the recovery rate of the acrylic acid of Comparative Example 2, which was calculated by a ratio of the flow rate of the acrylic acid in the lower discharge stream from the distillation column 300 to the flow rate of the acrylic acid in the reactor discharge stream, was 91.7%.

In this case, it was confirmed that since one cooling tower 120 was used and gas components were removed from the upper portion of the cooling tower 120, the amount of acrylic acid loss when the gas components were removed from the cooling tower 120 was increased as compared with Examples 1 and 2, and since the lower discharge stream from the cooling tower 120 was split and separately supplied to the extraction column 200 and the distillation column 300 so that the content ratio of water to the acrylic acid in the stream supplied to the extraction column 200 and the distillation column 300 was not able to be controlled, the amount of acrylic acid loss when water was removed from the extraction column 200 was increased as compared with Examples 1 and 2.

The invention claimed is:

1. A method for preparing an acrylic acid, the method comprising:

supplying a lactic acid aqueous solution to a reactor and performing a dehydration reaction to prepare a reaction product including an acrylic acid;

supplying a reactor discharge stream including the reaction product to a first cooling tower and supplying an upper discharge stream from the first cooling tower to a second cooling tower;

supplying a first acrylic acid aqueous solution stream discharged from a lower portion of the second cooling tower to an extraction column;

supplying an upper discharge stream from the extraction column and a second acrylic acid aqueous solution stream discharged from a lower portion of the first cooling tower to a distillation column; and separating the acrylic acid from a lower discharge stream from the distillation column.

2. The method of claim 1, wherein a content ratio of water to the acrylic acid in the first acrylic acid aqueous solution stream is 3.0 to 4.5.

3. The method of claim 1, wherein a content ratio of water to the acrylic acid in the second acrylic acid aqueous solution stream is 1.0 to 2.1.

4. The method of claim 1, wherein the upper discharge stream from the extraction column and the second acrylic acid aqueous solution stream form a mixed stream and the mixed stream is supplied to the distillation column.

5. The method of claim 1, wherein gas components are separated to an upper portion of the second cooling tower.

6. The method of claim 5, wherein the gas components include acetaldehyde.

7. The method of claim 1, wherein an extractant is supplied to the extraction column, and the extractant is discharged as an upper discharge stream from the extraction column, supplied to the distillation column, separated to an upper portion in the distillation column, and circulated to the extraction column.

8. The method of claim 1, wherein water is separated as a lower discharge stream from the extraction column.

9. The method of claim 1, wherein water is separated as a side discharge stream from the distillation column.

10. The method of claim 1, wherein a content ratio of water to the acrylic acid in the reaction product is 2.0 to 3.5.

11. The method of claim 1, wherein operation temperatures of the first cooling tower and the second cooling tower are 40° C. to 200° C., respectively, and operation pressures thereof are 1 kg/cm$^2$ to 20 kg/cm$^2$, respectively.

* * * * *